(12) United States Patent
Montanari et al.

(10) Patent No.: US 6,479,059 B2
(45) Date of Patent: Nov. 12, 2002

(54) TRICHOLOGICAL LOTION FOR TOPICAL USE

(75) Inventors: Daniela Montanari, Padua (IT); Manuela Guglielmo, Vigonovo (IT)

(73) Assignee: Gecomwert Anstalt, Vaduz (LI)

( * ) Notice: Subject to any disclaimer, the term of this patent is extended or adjusted under 35 U.S.C. 154(b) by 0 days.

(21) Appl. No.: 09/738,345

(22) Filed: Dec. 18, 2000

(65) Prior Publication Data

US 2001/0003583 A1 Jun. 14, 2001

Related U.S. Application Data

(63) Continuation of application No. PCT/EP99/04294, filed on Jun. 21, 1999.

(30) Foreign Application Priority Data

Jun. 22, 1998 (CH) ................................................ 1330/98

(51) Int. Cl.$^7$ ................................................ A61K 7/06
(52) U.S. Cl. ................... 424/401; 424/70.1; 424/70.51; 514/2; 514/8
(58) Field of Search ................................ 424/401, 70.1, 424/70.51, 70.122; 514/212, 8, 2

(56) References Cited

U.S. PATENT DOCUMENTS

| | | | |
|---|---|---|---|
| 5,086,040 A | | 2/1992 | Bonfils et al. ................... 514/8 |
| 5,229,266 A | * | 7/1993 | Heng .......................... 435/7.2 |
| 5,641,508 A | * | 6/1997 | Li et al. ...................... 424/450 |
| 5,972,929 A | * | 10/1999 | Kobayashi et al. .......... 514/212 |

FOREIGN PATENT DOCUMENTS

| | | | |
|---|---|---|---|
| FR | 2609393 | * | 2/1988 |
| WO | A-98 18432 | | 5/1998 |

* cited by examiner

*Primary Examiner*—Jose' G. Dees
*Assistant Examiner*—M. Haghighatian
(74) *Attorney, Agent, or Firm*—Daniel J. O'Byrne

(57) ABSTRACT

The present invention concern a cosmetic composition for topical application for reactivating the physiological growth of hair, said composition comprising a synergistic association of cysteine, lysine or derivatives thereof, with a glycoprotein, in a physiologically acceptable vehicle.

9 Claims, 9 Drawing Sheets

TRICHOLOGICAL LOTION FOR TOPICAL USE

CROSS-REFERENCE TO RELATED APPLICATIONS

This application is a continuation of application number PCT/ EP99/04294 filed on Jun. 21, 1999.

BACKGROUND OF THE INVENTION

The present invention relates to a cosmetic composition for topical application for reactivating the physiological growth of hair in regions affected by thinning in which there are follicles that have not fully atrophied.

Specifically, the present invention relates to a cosmetic composition in lotion form which is suitable for topical application to the scalp in order to improve the aesthetic appearance of the hair that is present and to make hair grow thicker in the areas where thinning caused by androgenic alopecia and/or defluvium has occurred.

Lotions and preparations against hair loss, based on active principle which improve the trophism of the scalp and reactivate hair follicles, have long been known.

Currently commercially available preparations for trichological use generally include rubefacient substances, vitamin compositions and derivatives thereof, usually in association with suitable nutrient compounds.

Among the various commercially available preparations, a hair loss prevention preparation based on Nicotenil, an association of three active ingredients, benzyl nicotinate, monomethyl silanetriol methionate and panthenol, is known since 1989. The topical application of this preparation to the scalp stimulates blood circulation, which by conveying a surplus of nutrient substances to the root of the hair reduces and limits hair loss.

Moreover, a hair loss treatment preparation has been known since 1991 which is based on the association of three active principles whose activity stimulates the hair follicles: sodium lauroyl cysteine, lysine hydrochloride and Nicotenil.

This preparation, when administered locally on the scalp of patients affected by androgenic alopecia, has proved itself effective in reducing hair loss.

Cosmetic preparations of the prior art, though having been found to be effective in slowing down hair loss, have not proved able to effectively make hair grow thicker on the treated scalp and to produce a visually appreciable increase in shaft diameter.

Formulations based on a pharmacologically active principle, minoxidil, are also currently commercially available: minoxidil had been used in the treatment of arterial hypertension and it was unexpectedly found to be effective in causing the regrowth of hair in subjects affected by androgenic alopecia.

Although the daily and prolonged administration of formulations based on minoxidil has proved effective in the treatment of various forms of hair loss and in significantly stopping hair loss, it suffers the drawback of causing in a significant percentage of the treated subjects a variety of side effects, such as allergic skin reactions, hirsutism, drops in arterial pressure and headache.

In the current state of the art, therefore, the need is felt to have new and effective trichological preparations whose formulations are not based on active principles that have an intense activity from the pharmacological point of view and therefore induce dangerous side effects.

SUMMARY OF THE INVENTION

One of the aim of the present invention is to provide a cosmetic-trichological composition useful to reactivate a physiological growth of hair in regions affected by thinning and to produce structural and morphological changes in the hair which can be appreciated from a cosmetic point of view.

Another object of the present invention is to provide a cosmetic composition for local application to the scalp which slows down the hair loss and makes said hair grow thicker, and the use of which entails essentially no side effects of the systemic kind.

A further object of the present invention is to provide a cosmetic composition in lotion form for trichological use which is simple to use and does not have high production costs.

In view of this aim, these objects and others which will become apparent hereinafter, a composition for topical application for reactivating physiological hair growth is provided, according to a first aspect of the invention, which comprises an association of cysteine, lysine and/or derivatives thereof with a glycoprotein in a physiologically acceptable carrier.

Cysteine is a sulfur-containing amino acid whose presence in the biochemical process for keratin synthesis is essential. Cysteine is in fact rich in —S—S— disulfide bridges which constitute the bond that keeps together the polypeptide chains of keratin, which is a key protein of hair structure.

When applied locally, the cysteine that is present in the formulation according to the invention partly fixes to the keratin structure of the hair, reinforcing its shaft, and is partly absorbed by the subcutaneous region of the scalp, thus helping to reduce and control the increased sebaceous secretion of the scalp that often accompanies hair loss processes.

Within the scope of the present invention, the term "cysteine derivative" designates the salts, esters or complexes thereof with other physiologically acceptable substances.

A particularly suitable cysteine derivative is sodium lauroyl cysteine.

Lysine is an essential amino acid which promotes cell regeneration in the body and is an indispensable element for the physiological growth of the body. A lysine deficit in fact results in stop of growth, protein deficit and a reduction in the keratinization process.

The use of lysine or of a derivative thereof in the formulation of the composition according to the invention has proved fundamental, at the level of the internal sheath of the root, for forming of lysine-glutamine bonds between polypeptide chains which help to increase substance and shape and the hair.

The expression "lysine derivative" is used in the description and in the claims to designate its salts, esters or complexes with other physiologically acceptable substances.

Within the scope of the present invention, a particularly suitable and active form of lysine derivative is lysine hydrochloride.

Surprisingly, it has now been found that the association of a glycoprotein, a molecule characterized by the presence of a glucidic fraction and of a protein fraction, with the above-described active principles produces a synergistic effect on hair regrowth and structure.

The presence of the glucidic fraction in the molecule is believed to be essential in the formulation according to the invention because it increases cell cohesion by forming intercellular bridges and induces specific biological activities similar to hormone and enzyme activities.

It has been found that the addition of a glycoprotein to the cysteine and lysine considerably increases the rate of utilization of the first two active principles in the biosynthesis of keratin.

Keratin is a substance which has a high relative molecular mass, has a protein-fibrous nature and is constituted by a group of polypeptide chains originating from the condensation of amino acids. Keratin polypeptides are orientated so as to be parallel to the longitudinal axis of the shaft of the hair and the —S—S— disulfide bonds that form between two cysteine molecules are characteristic of the keratin structure.

The local administration at the level of the scalp of lysine and cysteine and/or derivatives thereof in association with a glycoprotein increases the formation of the polypeptide chains, adding both sulfide bonds and amino acids, thus strengthening the keratin sheath and accordingly strengthening the shaft of the hair.

Within the scope of the present invention, among glycoproteins the family of lectins has been found to be particularly suitable for the preparation of a cosmetic-trichological composition.

Suitable lectins are both endogenous and exogenous in origin. The former are known as sarcolectins and have an active role in regulating cell proliferation, particularly by making cells sensitive to growth signals. The latter are present in the tissues of plants and can be easily extracted and purified.

According to a preferred embodiment of the invention, a lectin extracted from Solanum tuberosum L. is used which advantageously has a relative molecular mass of approximately 20,000 daltons. Lectin extraction and purification techniques are of a known type and are used commonly in the field of plant chemistry.

The inclusion of a glycoprotein in the formulation of the composition of the invention, particularly a lectin, produces a stimulation of cellular respiration which leads to an activation of cell metabolism processes.

It has now been noted unexpectedly that the association of said glycoprotein with cysteine and lysine or derivatives thereof produces a synergistic effect of hair growth stimulation which can be explained only partially by an increase in the cellular respiration.

In particular, it has been found surprisingly that the simultaneous administration of said three active principles causes an increase in the oxygen consumption with respect to basal conditions. This unexpectedly large increase is combined with a considerable increase in the biosynthesis of the keratin structures of the hair.

The data obtained from in vitro tests conducted on cell lines of human fibroblasts and keratinocytes has further produced results, in terms of cell proliferation, which indicate a synergistic effect of the three base components of the composition according to the invention.

According to one embodiment of the present invention, the cosmetic composition is in the form of a water-based solution suitable for topical application.

According to a preferred embodiment, the composition according to the invention comprises an additional active principle which is constituted by nicotinic acid or an ester thereof, conveniently the benzyl ester (benzyl nicotinate).

The topical application of a nicotinic acid ester simultaneously with the three basic active principles of the formulation according to the invention produces local vasodilatation with a temporary increase in blood flow at the capillary level, accompanied by a modest erythema and a slight temperature increase.

In particular, the topical administration of benzyl nicotinate, conveniently as a water-alcohol solution, increases the supply of oxygen and nutrients at the level of the hair follicle and increases their absorption by the hair bulb.

According to another embodiment, the composition for topical use according to the invention further includes a phospholipid, a highly liposoluble molecule which acts as an active carrier.

Phospholipids are ubiquitous molecules which are present in high concentrations at the cell membrane level and in endogenous lipoproteins and have an active role in several metabolic and biochemical processes, such as cellular oxidative phosphorylation, mitosis, intra/extracellular ion transport, chromosome replication and others.

In view of their structure, phospholipids possess a high affinity for the membrane of epithelial cells, allowing the exchange and penetration of the active principles through said membrane.

The presence of a phospholipid in the formulation of the composition according to the invention performs a dual action, acting as carrier of the included active principles and as an agent which facilitates their penetration through cell membranes.

One phospholipid found to be particularly suitable for the application according to the present invention is phosphatidylcholine, a lecithin derivative, esterified with choline.

Phosphatidylcholine is conveniently subjected to a preliminary treatment in order to increase its solubility in water and its stability in a water-alcohol solution, making it particularly suitable for the formulation of compositions according to the invention.

This preliminary treatment comprises the mixing of three components: phosphatidylcholine, butylene glycol and water, preferably at a temperature between 30 and 50° C., more preferably at approximately 40° C., followed by cooling to ambient temperature of the resulting mix, and by filtration thereof. According to a preferred embodiment, said three components are mixed in the following weight ratios: 8 to 12% phosphatidylcholine by weight; 40 to 60% butylene glycol by weight; 40 to 60% water by weight.

The mixing step conveniently lasts approximately 4 to 5 hours.

At the end of the treatment, a solution is obtained which is highly soluble in a water-alcohol solution with a percentage of ethyl alcohol generally between 50 and 60%.

Advantageously, this last solution is added, preferably in an amount equal to 0.05% by weight, to one of the compositions according to the invention.

One embodiment of the composition according to the invention comprises the following principles which are active in stimulating hair regrowth:

cysteine, lysine or derivatives thereof (lysine hydrochloride and sodium lauroyl cysteine), glycoprotein (lectin), nicotinic acid ester (benzyl nicotinate) and phospholipid (phosphatidylcholine).

Additional active principles which stimulate hair growth, advantageously selected from the group consisting of methionine and derivatives thereof, biotin, silanediol salicylate and mixture thereof, can be incorporated in the composition of the present invention to further increase the hair growth stimulation.

The expression "methionine derivative" designates a salt and/or ester thereof with physiologically acceptable compounds. Zinc acetyl methionate is particularly suitable.

Biotin is preferably included in formulations of the composition according to the invention which are specific for the treatment of forms of alopecia affecting female subjects.

The composition for topical use according to the invention can also comprise additives conventionally used in trichological preparations, such as preservatives, stabilizers, antibacterial agents, emulsifiers, buffers and colours. In particular, when the composition is in the form of a solution, preferably 0.04% by weight is added of a dyeing solution based on a brown dyeing or pigment. Said dyeing solution is made making a 50% dilution with water of a water-based solution including 5% by weight of a physiologically acceptable dyeing or dyeing mixture. Advantageously, said dyeing or pigment is a mixture of CI 19140-14720-16255-73015-28440.

As a vehicle for the composition according to the invention it is possible to use a water-alcohol solution which advantageously includes glycol, and excipients commonly used in techniques for preparing cosmetic preparations for local application.

By way of example, it is possible to use as excipients glycerine, disodium EDTA, triethanolamine, menthol, benzophenone, and physiologically acceptable carriers and colors.

According to another aspect, the present invention provides a method for preparing a trichological composition, preferably in the form of a solution (lotion), which comprises the dissolving of the water-soluble fractions in water and of the remaining fractions in alcohol solvent, followed by the blending of the two fractions while mixing.

The resulting mixture is then buffered in order to reach a pH range (between 6 and 6.8) which is compatible with the pH of the skin and is filtered and then packaged in suitable containers, such as vials and bottles.

According to another aspect, the present invention relates to the use of a synergistic trichological composition which comprises a glycoprotein, cysteine and lysine and/or derivatives thereof to produce a preparation for stimulating hair regrowth.

The simultaneous use of these three active principles produces a synergistic effect of stimulation of the hair follicles that are not fully atrophied, helping to restore the optimum physiological conditions for hair growth.

The inclusion in the formulation of a fourth active ingredients which is constituted by nicotinic acid or ester thereof, such as benzylnicotinate, is preferred.

Use according to this last aspect of the invention provides for the application of a cosmetically effective amount of the composition according to the invention directly on the scalp, preferably once a day or every other day.

The composition can be applied locally, in the regions where the hair is thinning, one or more times a day, preferably following treatment cycles lasting 2 to 3 months alternated with a rest period.

According to another aspect of the present invention, a cosmetic treatment method is provided which comprises the local application, at the scalp level, of a cosmetically effective amount of a composition of the above described type.

The effectiveness on hair regrowth and the local tolerability of a composition in lotion form cited in example 3 has been evaluated clinically and by means of noninvasive instrumental investigations.

The treatment was conducted on the scalp of subjects affected by hair thinning caused by forms of androgenic alopecia and/or defluvium and showed no side effects of the systemic type.

The treatment entailed the application of an amount of lotion sufficient to wet the surface of the scalp, advantageously every other day, for a period of preferably 90 days.

Instrumental measurements (sebum, hydration and pH) and clinical evaluations were performed in basal conditions one, two and three months after the beginning of the treatment.

The following main parameters were considered:
1) degree of alopecia and defluvium
2) degree of seborrhea on the scalp and on the shaft of the hair
3) appearance of the dandruff
4) pull test In basal conditions and at the end of the treatment, the area of the skin subjected to the electronic counting of the hairs in the growth phase was shaved and photographed; an alopecia-affected area (insertion line of the hair along the right frontoparietal region) was photographed; and hair samples were taken for morphological evaluation by optical microscope (state of the bulb, state of the shaft, thickness and sheen of the shaft).

The study was conducted on a sample of 25 subjects, 14 female and 11 male, aged between 23 and 45, affected by grade I–II androgenic alopecia according to Ludwig's scale for the women and by grade II–III alopecia according to Hamilton's scale for the men, and or defluvium.

BRIEF DESCRIPTION OF THE DRAWINGS

The results obtained are summarized in the charts shown in FIGS. 1 to 9, wherein.

DESCRIPTION OF THE PREFERRED EMBODIMENTS

Figure 1:
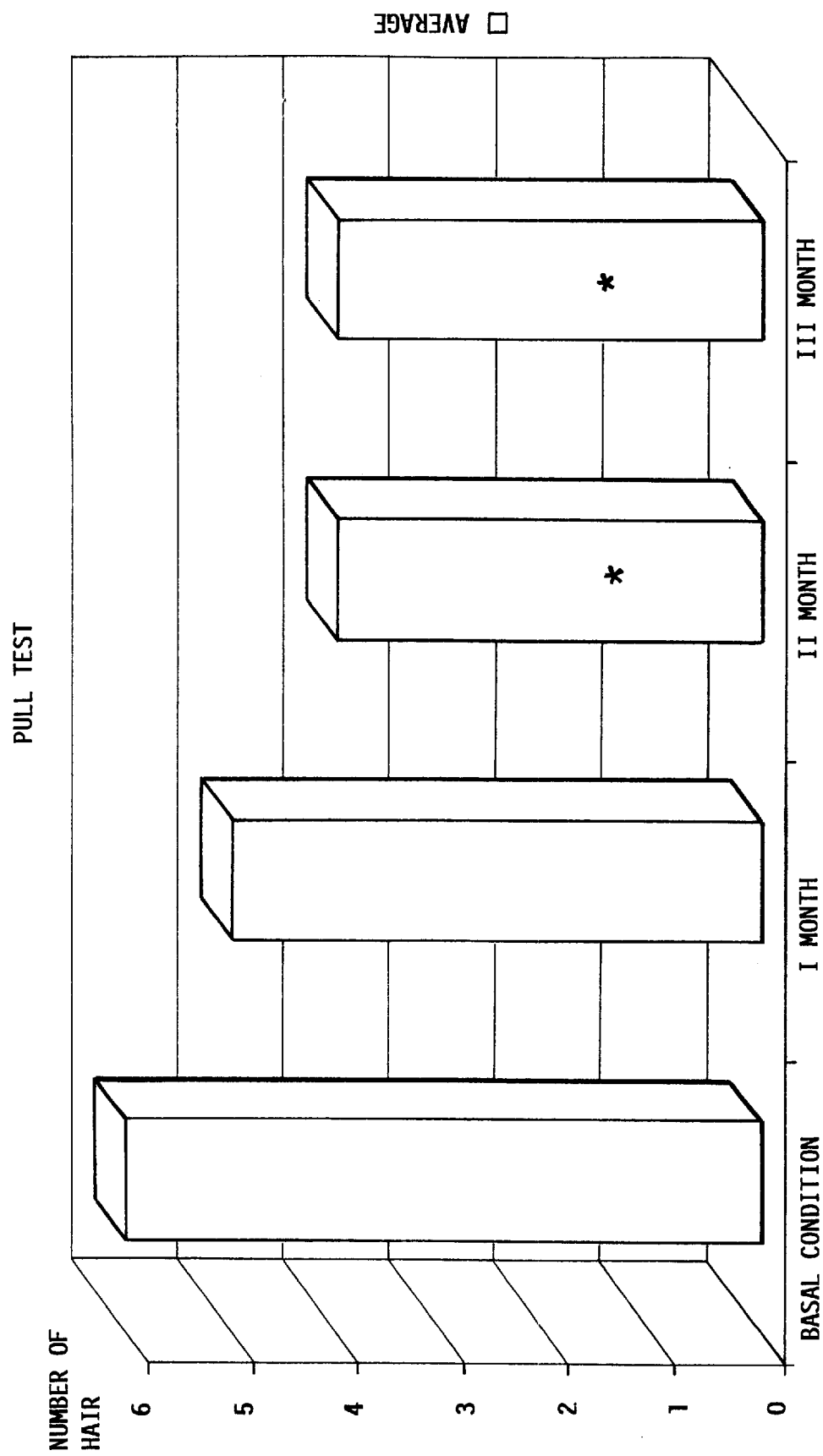
FIG. 1 shows bar charts of the average results of the pull test conducted on the treated subjects. Four charts are presented which relate to the basal situation and to the condition after 1, 2, 3 months of treatment with the composition according to the invention.

FIG. 1 indicates that the cosmetic treatment induces a statistically significant reduction ($P<0.05$; Bonferroni test), equal to 33% of the hairs removed by pull test with respect to the basal value, indicating an increase in resistance to traction.

Figure 2:
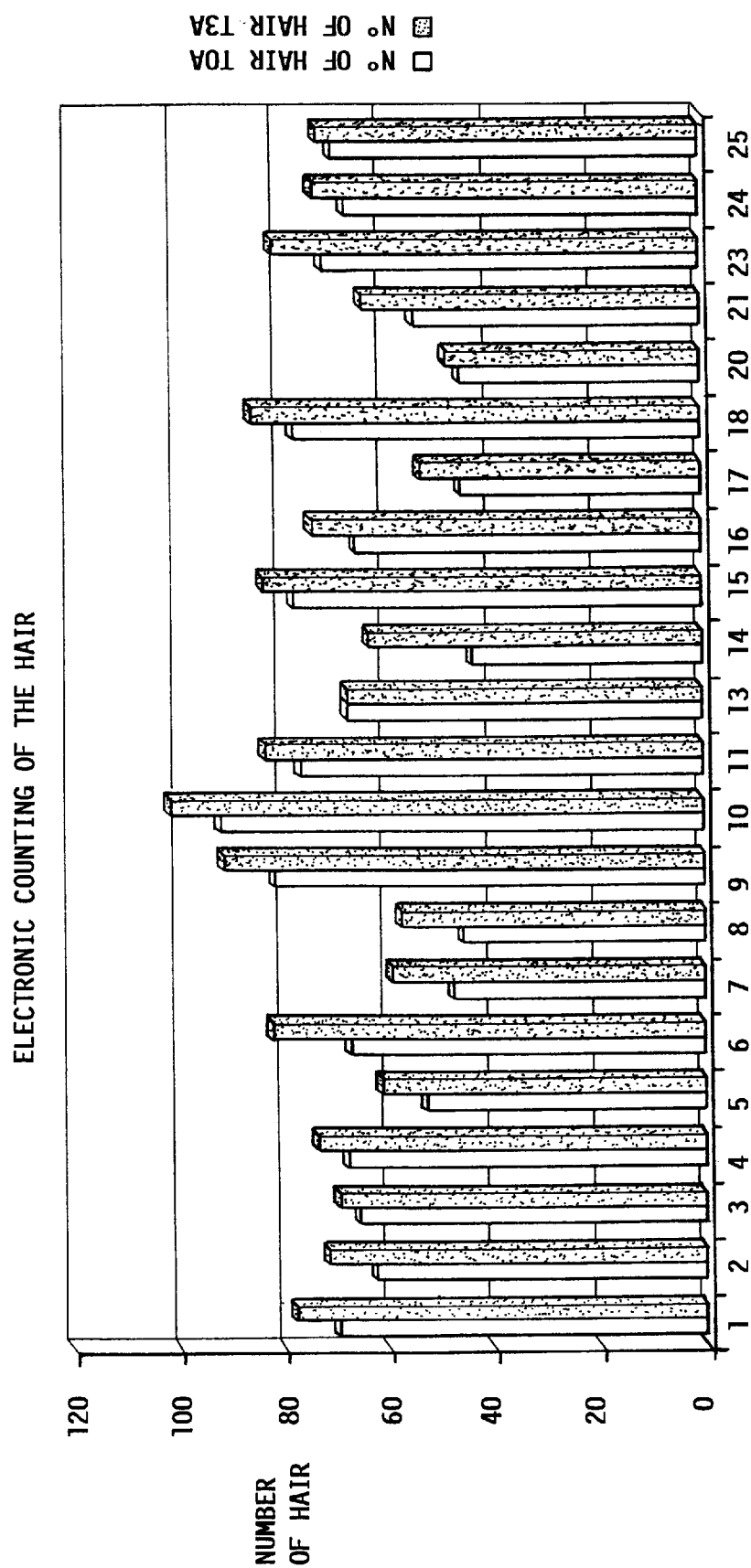
FIG. 2 shows bar charts of the results found in the electronic counting of the hairs in basal conditions and after the treatment.
Figure 3:
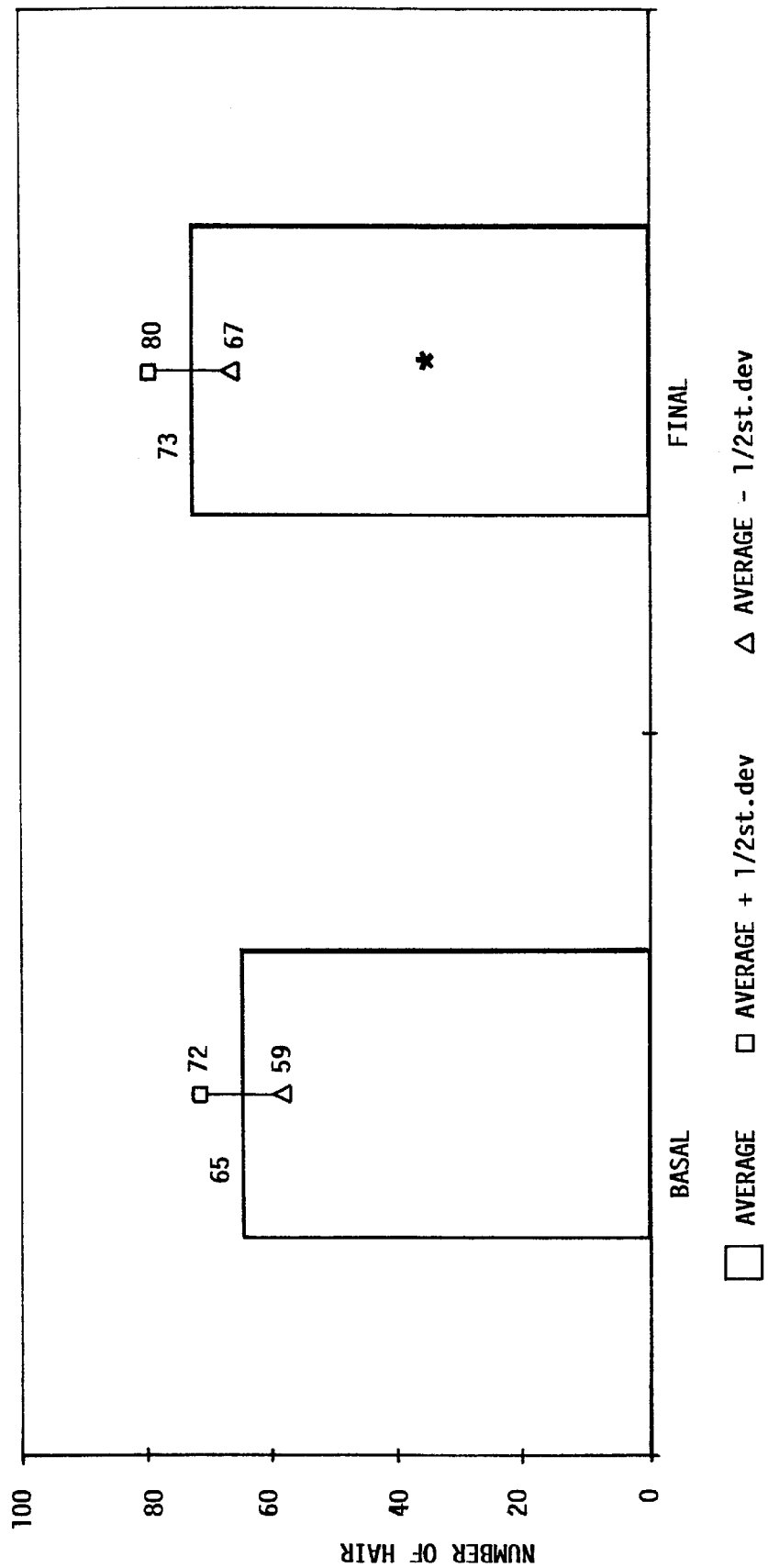
FIG. 3 shows bar charts of the average values of the individual results plotted in FIG. 2.

The data summarized in the charts of FIGS. 2 and 3 indicate that after a three-month period there occurred a statistically significant average increase ($P<0.001$; Student's test t), equal to 13% with respect to the basal value, in growing hairs evaluated by electronic counting.

Electronic counting of the number of hairs was performed by shaving an area of the scalp located on the vertex and measuring 1 $cm^2$. In order to subsequently identify the shaving of the same region without error at the different times (1, 2, 3 months), an area was determined with the aid of a cardboard cutout, starting from three coordinates constituted by the tip of the nose and the tip of the auricles. An electronic landmark was fixed on the images obtained for electronic counting. This area was photographed immediately after shaving and 5 days later. In this manner it is possible to electronically count the hairs in the active growth phase by computerized image analysis. The digitized images for electronic counting were acquired at the times T0A and T3A for each individual subjected to the cosmetic treatment.

Figure 4:
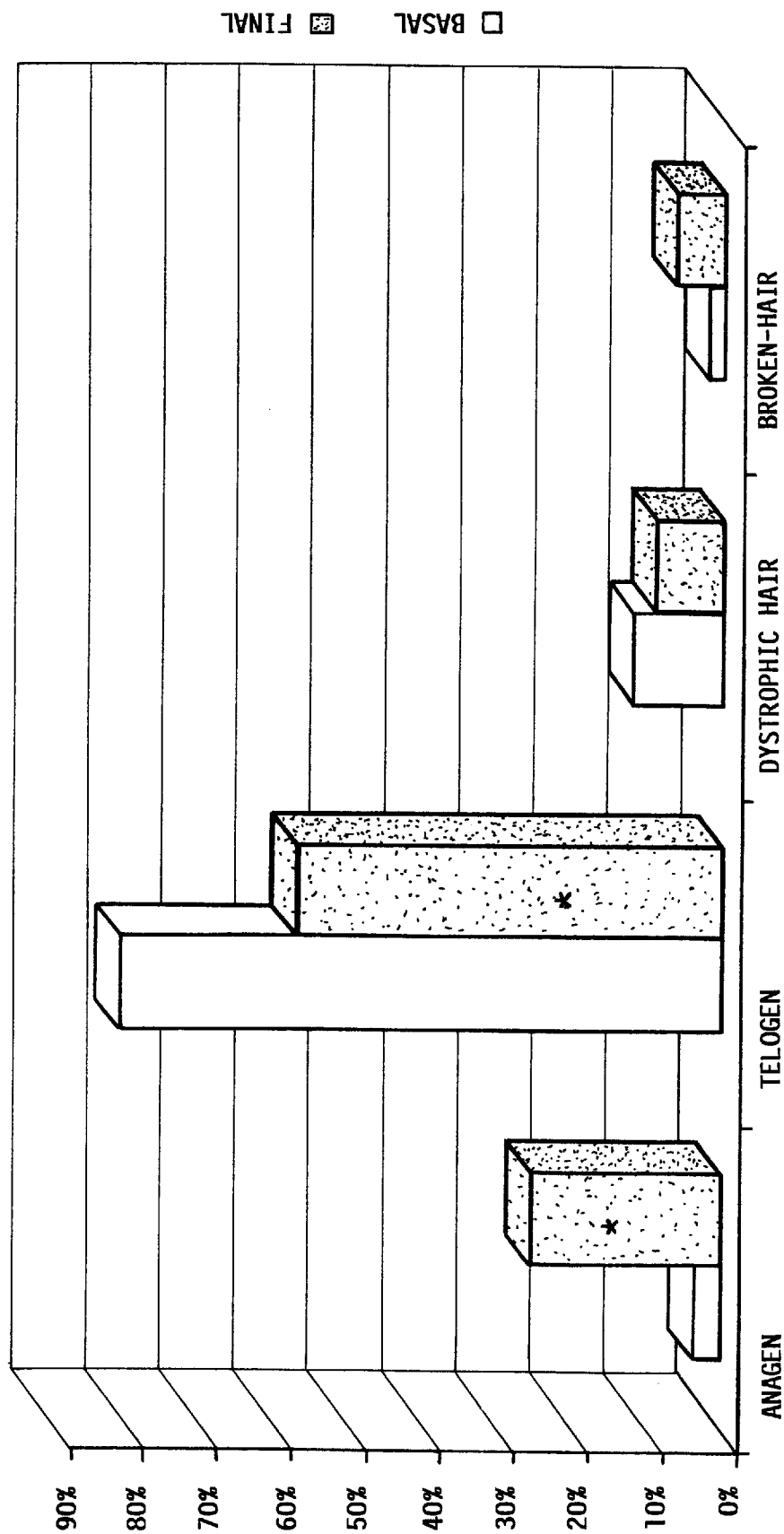
FIG. 4 shows bar charts of the percentage variations in the morphological conditions observed at the level of the hair bulb in the treated subjects, in the basal and final conditions.

FIG. 4 illustrates the morphological variations at the level of the bulb, observed by optical microscope. Bulb analysis showed an increase in the bulbs in the anagen phase, i.e., in the phase of new hair growth (from 3.7 to 25.9% of the total removed bulbs) and a reduction in the bulbs in the telogen phase (from 81.5% to 57.7% of the total removed bulbs), which were statistically significant ($P<0.05$; Student's test t).

Figure 5:
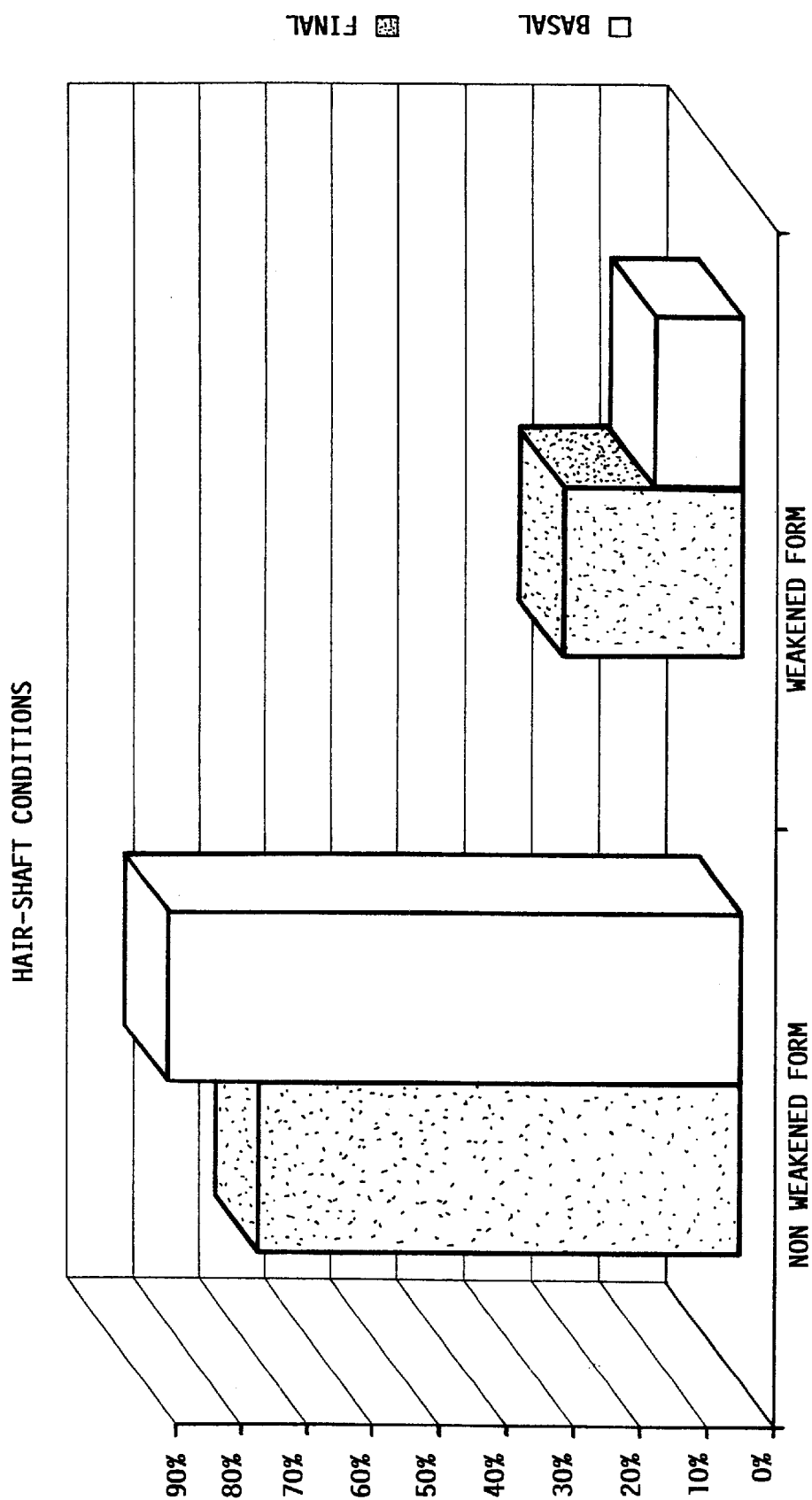
FIG. 5 is a bar chart of the percentage variations of the hairs in weakened form and non-weakened form, in basal conditions and after the treatment.

FIG. 5 shows the variations observed also at the level of the shaft of the hair following the cosmetic treatment according to the invention.

The variations at the level of the bulb and in the diameter of the shaft of the hair were determined by evaluation with an optical microscope.

First of all, a region of the scalp adjacent to the thinning area was selected. Then traction was applied until a sample composed of approximately ten hairs was obtained. The removed hair samples were collected in a transparent plastic bag. For microscopic analysis, the hairs were placed on a slide. If the hairs were longer than the slide, the part of the hairs that protruded from said slide was cut and then mounted on another slide. A second slide was placed on the first one and joined to it with adhesive tape at its ends. The shaft was examined along its entire length at low magnification (×40) and at a higher magnification (×100 and ×400), whereas bulb and end examination was performed at a higher magnification (×100 and ×400). The following characteristics of the shaft were considered: state of the external sheath, uniformity and ruptures, if any, of the shaft. The characteristics of the bulb allowed to identify the phase of the hair (anagen, telogen). In the anagen phase, there is a dark end portion (the bulb) followed by a central dark long part (the shaft), surrounded by the internal sheath of the root. In the telogen phase, the end part of the shaft resembles a pad, the portion of the bulb is not pigmented and does not have the internal sheath of the root. The dystrophic bulb has a hook-like or deformed appearance and the sheaths may be absent, but it maintains the characteristic pigmentation of the anagen phase and is the result of traction during removal of the hair.

Figure 6:
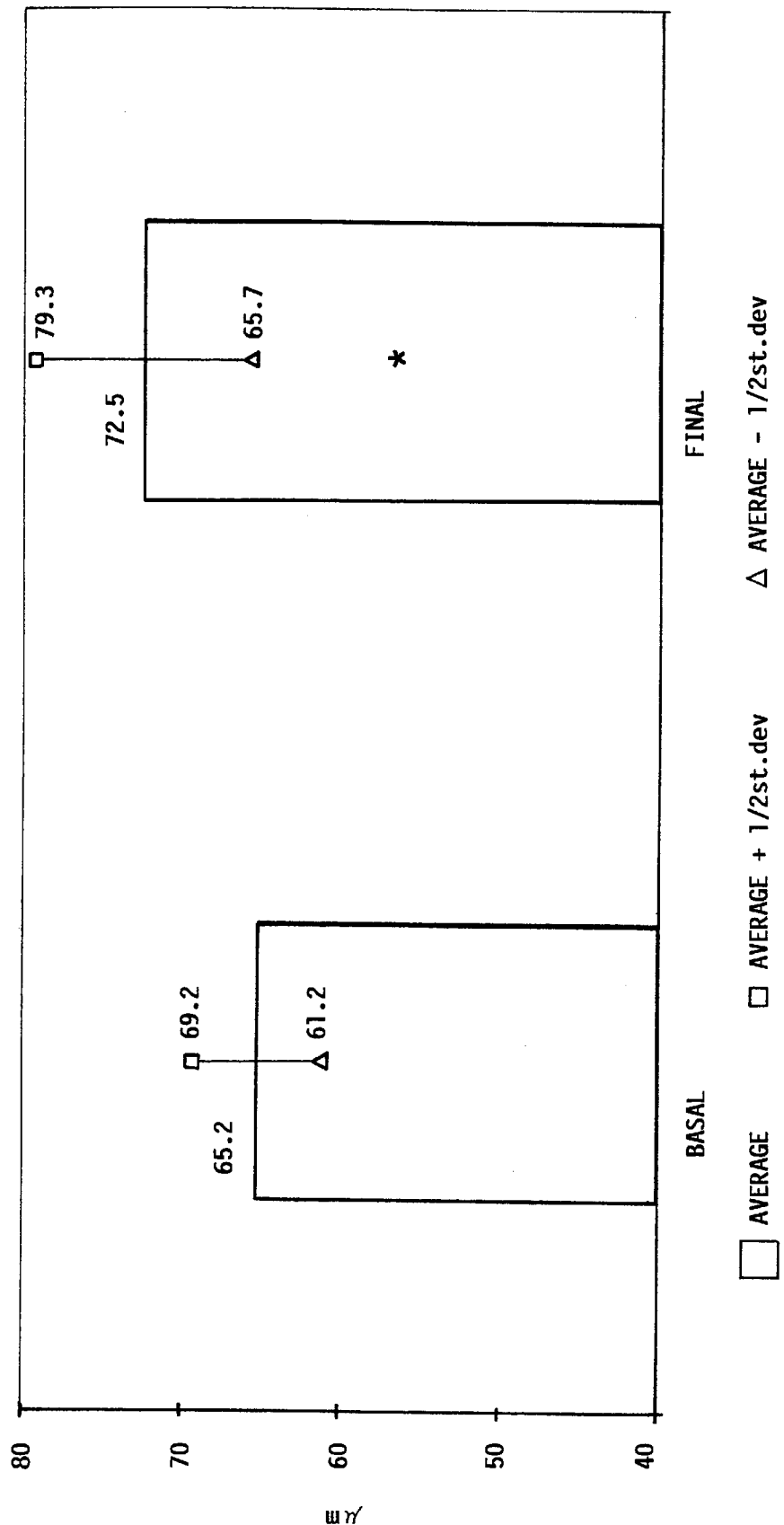
FIG. 6 is a bar chart of the average variation of the diameter of the hairs of the treated subjects, in the basal condition and at the end of the treatment.

FIG. 6 shows that the cosmetic treatment determines, in subjects treated for three months, an increase in hair diameter which is significant from the cosmetic point of view. In particular, morphometric analysis of the hairs has shown an average increase of the diameter of 11.2% with respect to basal conditions. The thickness of the shaft was measured by acquiring a computerized magnified image of the hair.

Figure 7:
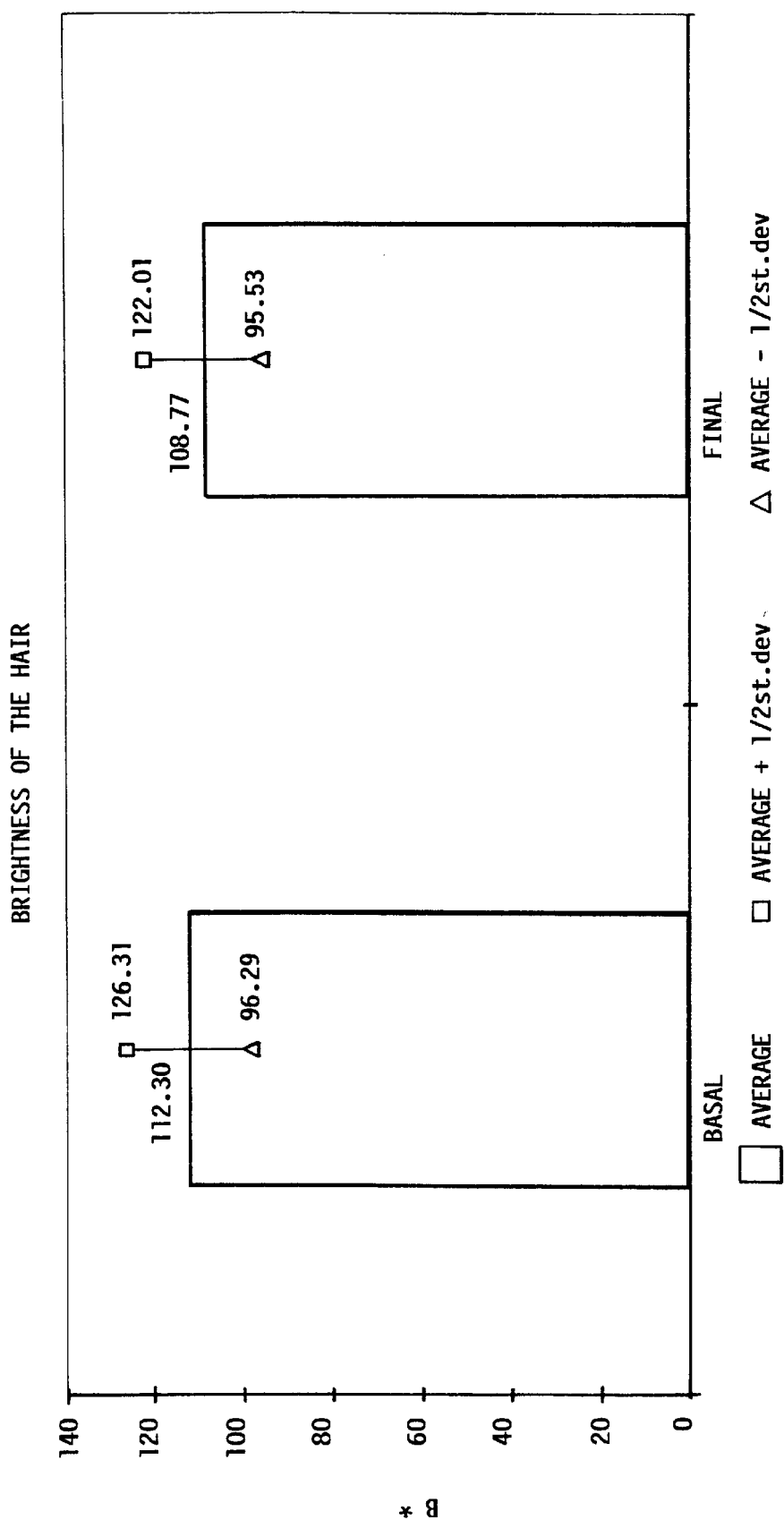
FIG. 7 is a bar chart of the average variation of the brightness of the hairs of the treated subjects, in the basal condition and at the end of the treatment.

FIG. 7 shows that the brightness of the hairs of the individuals subjected to the treatment does not vary to a particularly appreciable extent. In order to perform sheen measurement, the L parameter according to the CIE standard (Commission Internationale de l'Eclairage L a b; 1976) was used as reference.

Figure 8:
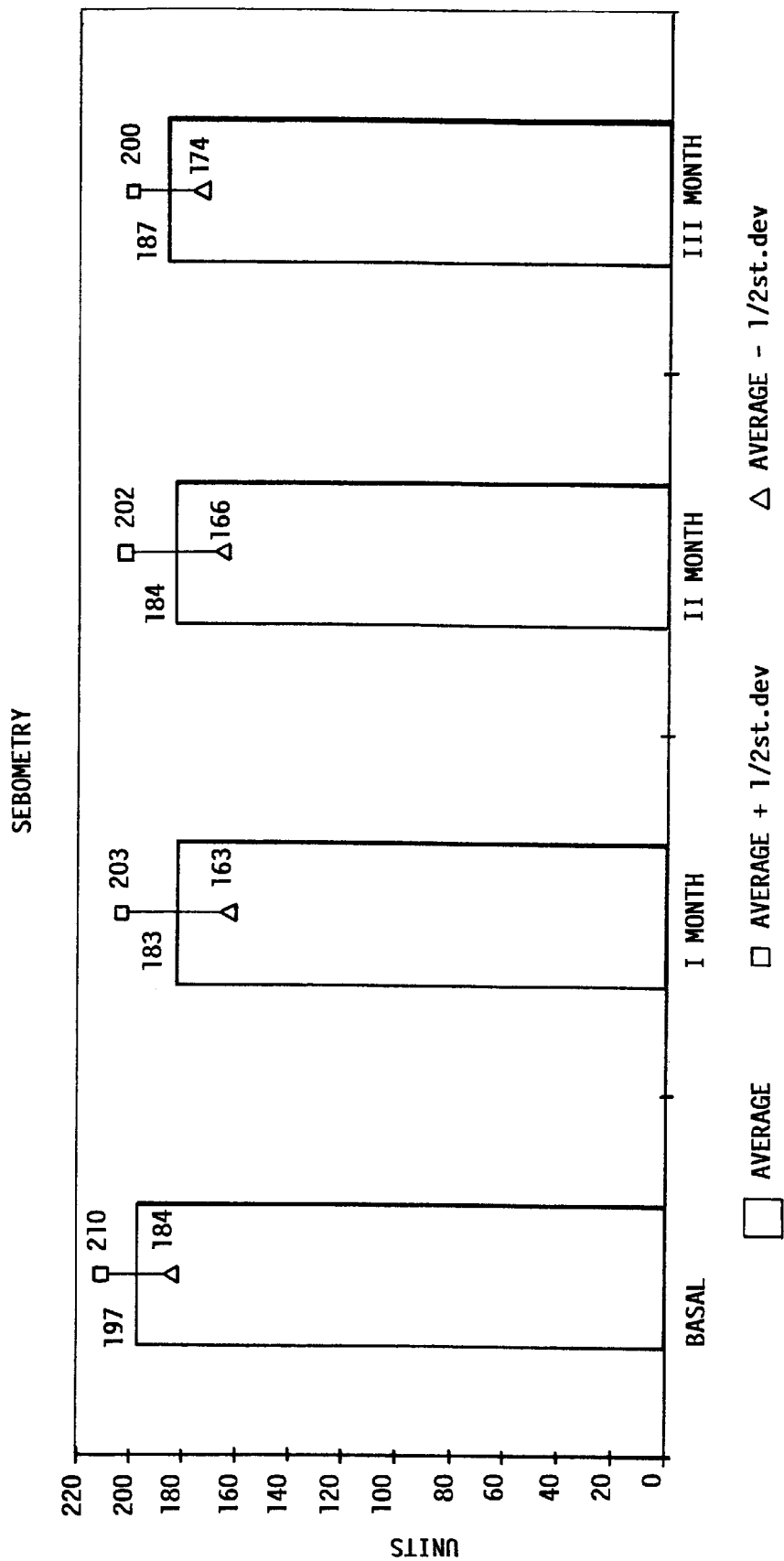
FIG. 8 is a bar chart of the average variation in the sebum measurements of the hairs of the treated subjects in the basal condition and after 1, 2, 3 months of treatment.

FIG. 8 shows that after three months of treatment there is a modest reduction in the amount of sebum produced by the sebaceous glands of the scalp. This reduction leads to an aesthetic improvement of the hair of the treated subject.

The Skin Tester device (IMS, Haifa), constituted by an opaque glass surface mounted on a spring-loaded slider, was used to determine sebum values. The measurement was performed by resting the probe against the skin, by means of a pressure kept constant by the spring-loaded mechanism, for a few seconds and then returning the sensor to its seat. The apparatus is thus able to read the photometric variation in opaque surface transmittance after contact with the skin. The variation in the transparency of the surface of the probe is proportional to the amount of lipids present on the surface of the skin. The value obtained on the display of the device is inversely proportional to the amount of lipids collected by the probe.

Figure 9:
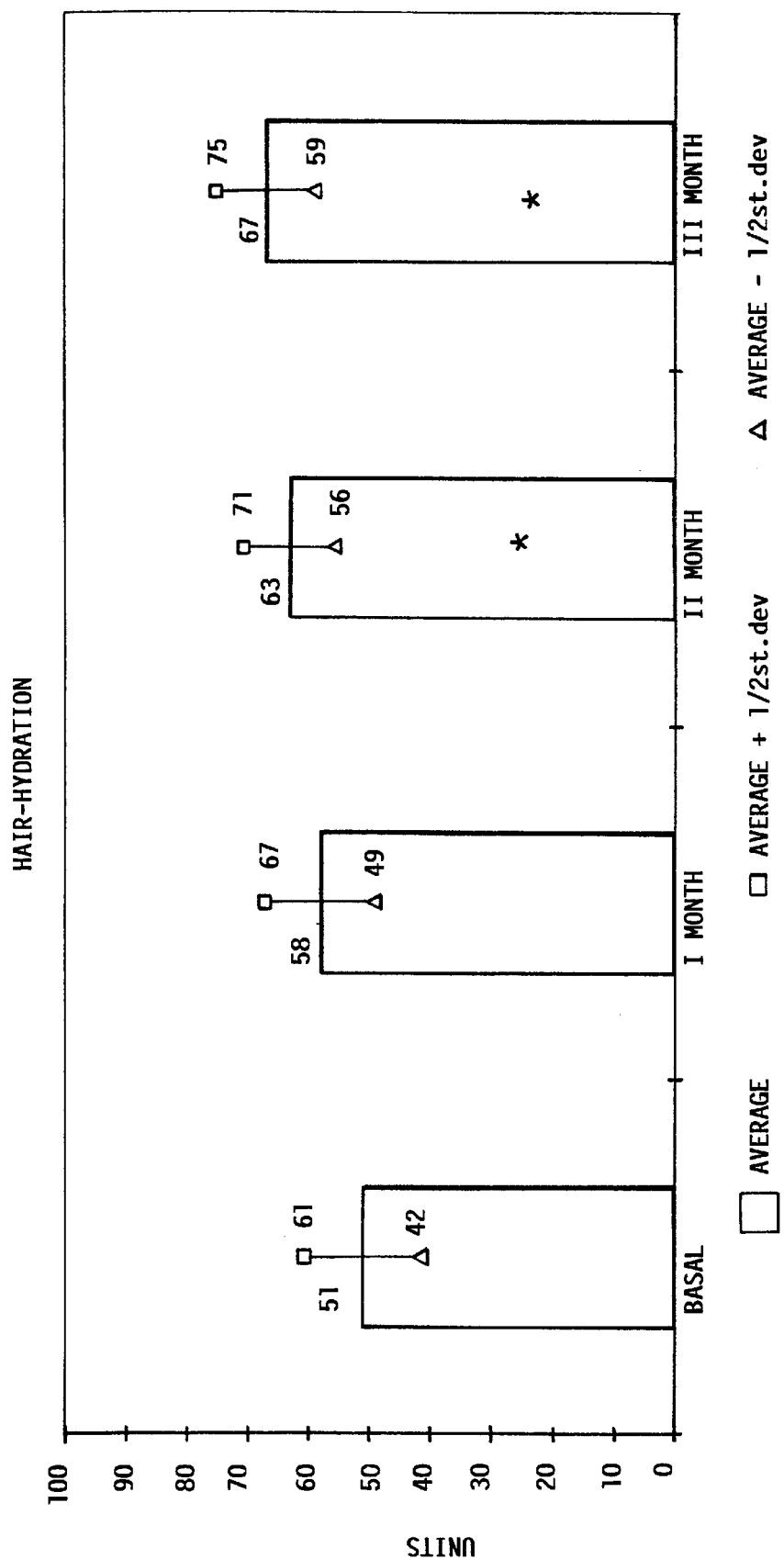
FIG. 9 is a bar chart of the average variation of the hydration of the hairs of the treated subjects, in the basal condition and after 1, 2, 3 months of treatment.

The cosmetic treatment according to the invention determines a statistically significant increase ($P>0.05$; Bonferroni test) in the level of cutaneous hydration, which is particularly evident when plotted as a bar chart (FIG. 9).

The cutaneous hydration level was tested by using a CM820 Corneometer (Courage-Khazaka, Köln, Germany) unit provided with a cylindrical sensor mounted on a spring-loaded slider and capable of performing capacitive electrical measurements. The measurements were performed by resting the sensor on the skin with a constant pressure which can be achieved thanks to the spring-loaded slider. The measurement principle is based on the fact that the dielectric constants of water and other materials are very different. A capacitor reacts with capacitance changes according to the water content when specimen tissues are placed within its measurement volume. The measurement of the capacitive properties of the surface of the skin is therefore an indirect expression of its degree of hydration. The value obtained on the display of the device is directly proportional to the water content of the surface of the skin.

EXAMPLE 1

Three types of formulation of the composition according to the invention, particularly suitable for topical application to male subjects, are given hereafter. The ingredients are provided by percentages by weight.

| INGREDIENTS | I | II | III |
|---|---|---|---|
| Silanediol Salicylate | 0.042 | 0.042 | 0.042 |
| Glicoproteins | 1 ppm | 2 ppm | 3 ppm |
| Zinc Acetylmethionate | 0.007 | 0.007 | 0.007 |
| Benzyl Nicotinate | 0.070 | 0.070 | 0.070 |
| Glutamine | | | |
| Lysine Hydrochloride | 0.074 | 0.084 | 0.098 |
| Biotin | | | |
| Sodium Lauroyl Cysteine | 1.260 | 1.440 | 1.680 |
| Butylene Glicol | 0.151 | 0.151 | 0.151 |
| Glycerin | 0.120 | 0.240 | 0.360 |
| Phosphatidylcholine | 0.005 | 0.005 | 0.005 |

-continued

| INGREDIENTS | I | II | III |
|---|---|---|---|
| Benzophenone-4 | 0.080 | 0.080 | 0.080 |
| Alcohol Denaturate | 51.600 | 51.600 | 51.600 |
| Menthol | 0.050 | 0.050 | 0.050 |
| Disodium Edta | 0.080 | 0.080 | 0.080 |
| Quaternium-52 | | | |
| 2-Bromo-2-Nitropropane-1.2-Diol | 0.012 | 0.012 | 0.012 |
| Triethanolamine | 0.032 | 0.032 | 0.032 |
| Cl 19140, Cl 14720, Cl 16255, Cl 73015, Cl 28440 | 0.001 | 0.001 | 0.001 |
| Water The balance | 100.00 | 100.00 | 100.00 |

EXAMPLE 2

Three types of formulation of the composition according to the invention, particularly suitable for topical application to female subjects, are given hereafter. The ingredients are provided by percentages by weight.

| INGREDIENTS | I | II | III |
|---|---|---|---|
| Silanediol Salicylate | 0.042 | 0.042 | 0.042 |
| Glicoproteins | 1 ppm | 2 ppm | 3 ppm |
| Zinc Acetylmethionate | 0.007 | 0.007 | 0.007 |
| Benzyl Nicotinate | 0.070 | 0.070 | 0.070 |
| Glutamine | 0.040 | 0.040 | 0.040 |
| Lysine Hydrochloride | 0.051 | 0.059 | 0.069 |
| Biotin | 0.020 | 0.020 | 0.020 |
| Sodium Lauroyl Cysteine | 0.882 | 1.008 | 1.176 |
| Butylene Glicol | 0.151 | 0.151 | 0.151 |
| Glycerin | 0.120 | 0.240 | 0.360 |
| Phosphatidylcholine | 0.005 | 0.005 | 0.005 |
| Benzophenone-4 | 0.080 | 0.080 | 0.080 |
| Alcohol Denaturate | 51.600 | 51.600 | 51.600 |
| Menthol | 0.050 | 0.050 | 0.050 |
| Disodium Edta | 0.080 | 0.080 | 0.080 |
| Quaternium-52 | 0.100 | 0.100 | 0.100 |
| 2-Bromo-2-Nitropropane-1.2-Diol | 0.012 | 0.012 | 0.012 |
| Triethanolamine | 0.032 | 0.032 | 0.032 |
| Cl 19140, Cl 14720, Cl 16255, Cl 73015, Cl 28440 | 0.001 | 0.001 | 0.001 |
| Water The balance | 100.00 | 100.00 | 100.00 |

EXAMPLE 3

The activity of a preparation for the topical application according to example 1 was subjected to a clinical evaluation. This research has been carried out for evaluating the effectiveness of the preparation in promoting the physiological hair growth.

A total of 10 men, aged 34 to 44, affected by alopecia were selected and treated in double-blind conditions for a 12 weeks. A preparation containing the composition according to the invention was topically applied on a part (SIde B) of the scalp, whereas on the other side (Side A) a lotion was applied which did not contain said active principle.

The effectiveness was clinically evaluated by means of controls carried out during and at the end of the research. All the subjects showed a greater growth increase at the side of the scalp treated with the product under examination. It should be noted that the action of the product under examination takes place at the level of the hair follicles still active.

The final evaluation made by the researcher for each subject of the test at the end of the treatment is as follows:

| Subject | Age | Final Evaluation |
|---|---|---|
| I | 36 | Very good result of the treatment. Evident signs of growth, particularly at side B. |
| II | 43 | Patient satisfied. Thicker hair is objectively observed, particularly at side B. |
| III | 41 | Good results of the treatment, particularly of that part of the scalp treated with lotion B. |
| IV | 38 | Treatment well tolerated, visible results of growth particularly at side B. |
| V | 36 | Treatment with good results: fairly good hair thickening, particularly with regard to side B. |
| VI | 44 | Very satisfied patient: good results both with regard to the hair loss and the signs of new growth. |
| VII | 35 | Treatment with good results: better growth. |
| VIII | 34 | Extremely good results: loss within the physiological extent, growth signs (more on side B) found, patient extremely satisfied. |
| IX | 45 | Treatment with good results. Growth signs present. |
| X | 35 | Very good results of treatment, both objective and subjective: little growth, better on side B. |

The disclosures in Swiss Patent Application No. 1998 1330/98 from which this application claims priority are incorporated herein by reference.

What is claimed is:

1. A cosmetic composition for topical application for reactivating the physiological growth of hair, comprising an association of an aminoacid selected from the group consisting of cysteine, lysine, and derivatives thereof with a glycoprotein, in a physiologically acceptable carrier.

2. A composition according to claim 1, further comprising a nicotinic acid ester.

3. A composition according to claim 2, wherein said nicotinic acid ester is benzyl nicotinate.

4. A composition according to claims 1, further comprising a phospholipid.

5. A composition according to claim 4, wherein said phospholipid is phosphatidylcholine.

6. A composition according to claim 1, further comprising an active ingredients selected from the group consisting of methionine, biotin, silanediol salicylate and mixtures thereof.

7. A composition according to claim 1, wherein it is in the form of a hydroalcoholic solution.

8. A composition according to claim 1, comprising: 0.05 to 5% benzyl nicotinate by weight; 1 to 50% sodium lauroyl cysteine by weight; 0.05% to 40% lysine hydrochloride by weight; 1 to 50 ppm glycoprotein; 0.001 to 1% phosphatidylcholine by weight in a hydroalcoholic vehicle.

9. A cosmetic treatment method, comprising the topical application of a cosmetically effective amount of a composition according to claim 1 on a scalp of a person on need of treatment.

* * * * *